United States Patent [19]

Vishnupad et al.

[11] Patent Number: 4,690,774
[45] Date of Patent: Sep. 1, 1987

[54] NOVEL TRANSLUCENT WATER IN OIL EMULSIONS

[75] Inventors: Mohan Vishnupad, Monroe; Jose E. Ramirez, Trumbull, both of Conn.

[73] Assignee: Chesebrough Pond's Inc., Greenwich, Conn.

[21] Appl. No.: 774,727

[22] Filed: Sep. 11, 1985

[51] Int. Cl.$^4$ .............................................. B01J 13/00
[52] U.S. Cl. .................................. 252/309; 514/873; 514/939; 514/941; 514/943
[58] Field of Search ................ 252/309; 514/939, 941, 514/943

[56] References Cited

U.S. PATENT DOCUMENTS

| | | | |
|---|---|---|---|
| 3,957,971 | 5/1976 | Oleniacz | 424/70 |
| 4,184,978 | 1/1980 | France et al. | 252/309 |
| 4,216,201 | 8/1980 | Calvo | 424/63 |
| 4,284,630 | 8/1981 | Yu et al. | 514/937 X |
| 4,407,824 | 10/1983 | Eckert | 514/939 X |
| 4,422,952 | 12/1983 | Koulbanis et al. | 252/309 |

FOREIGN PATENT DOCUMENTS 1127039 7/1982 Canada.

*Primary Examiner*—Richard D. Lovering
*Attorney, Agent, or Firm*—Morgan & Finnegan

[57] ABSTRACT

This invention relates to novel water in oil emulsions. The emulsions of this invention are translucent water in oil emulsions comprising a water phase containing a humectant, an oil phase comprising petroleum jelly and the like and an emulsifying agent to give a water in oil emulsion; the aqueous phase having a refractive index in essentially the same range as the oil phase.

The translucent water in oil of this invention have the same general appearance and feel of petroleum jelly and function like petroleum jelly but are superior thereto in the sense that when applied to skin will not only help prevent water from escaping therefrom or exist a barrier effect, but also, will allow water humectants and other moisturizers from the emulsion water phase to pass therethrough to contact the skin and to moisturize the skin.

The compositions of this invention are useful as skin moisturizer compositions. They may be used as a carrier or vehicle for oil and water soluble tropical drugs. They also may be used in the same general way as petrolatum (e.g. skin protectant agent, emollient, lubricant, etc.).

10 Claims, No Drawings

NOVEL TRANSLUCENT WATER IN OIL EMULSIONS

SUMMARY OF INVENTION

This invention relates to novel water in oil emulsions. The emulsions of this invention are translucent water in oil emulsions comprising a water phase containing a humectant, an oil phase comprising petroleum jelly and the like and an emulsifying agent to give a water in oil emulsion, the aqueous phase having a refractive index in essentially the same range as the oil phase.

The translucent water in oil emulsions of this invention have the same general appearance and feel of petroleum jelly and function like petroleum jelly but are superior thereto in the sense that when applied to skin will not only prevent water from escaping therefrom, but also will carry water and humectants and other moisturizers into the skin to moisturize the skin.

The compositions of this invention are useful as skin moisturizer compositions. They also may be used in the same general way as petrolatum (e.g. emollient, lubricant, etc.).

The novel translucent water-in-oil compositions are particularly useful as skin moisturizer compositions in the treatment of dry skin. Also contemplated are their use in wound healing ointments. The translucent water-in-oil emulsions of this invention also may be used in the same general way as petroleum jelly i.e. (1) dermatalogical uses as a skin emollient and lubricant to provide a soothing, softening and protective layer, and (2) long lasting lubricant for reducing friction between different types of surfaces, including metal and most plastic materials. The compositions of this invention are in medical compositions useful as carriers or vehicles for both oil soluble and water soluble drugs and like medicinal agents.

OBJECTS OF THIS INVENTION

An object of this invention is to provide novel translucent water in oil emulsions which not only have the appearance of petroleum jelly but also, like petroleum jelly acts as an occluding agent to prevent water from escaping from the skin.

A further object of this invention is to provide novel translucent water in oil emulsions which not only have the appearance of petroleum jelly and acts like it as an occluding agent to prevent water escaping from the skin, but also, unlike petroleum jelly will carry water and humectants and other moisturizers into the skin to moisturize the skin.

A still further object of this invention is to provide novel translucent water-in-oil emulsions which have the appearance of petroleum jelly but which are more economical to produce.

Another object of this invention is to provide a method for the production of novel translucent water-in-oil emulsions having the properties and attributes set forth in the foregoing objects.

GENERAL DESCRIPTION OF THE INVENTION

It has been found that the objects of this invention may be realized by forming a translucent water-in-oil emulsion comprising a water phase containing a humectant and any optional water soluble agents that may be present (e.g. coloring agents, preservatives, medical agents, agents to modify the refractive index), an oil phase comprising petroleum jelly and the like and any optional oil phase soluble additives including medicinal agents and agents to modify the refractive index and a water-in oil emulsifying agent, the aqueous phase having a refractive index in essentially the same range as the oil phase (i.e. 1.4 to 1.5, preferably 1.46 to 1.48, the refractive index of petroleum jelly being 1.47).

In the context of this invention the term "petroleum jelly and the like" as used herein means petroleum jelly (white petrolatum) or modified petroleum jelly wherein some of the petroleum jelly has been replaced by mineral oil. White petrolatum is a purified mixture of semi-solid hydrocarbons obtained from petroleum, chiefly of the methane series of the general formula $C_nH_{2N+2}$. The white to faintly yellowish unctuous mass has the density of 0.820–0.865, melting point of 38–54° C. and refractive index of 1.460–1.474.

In the translucent water-in-oil compositions of this invention the water phase contains water in amount from about 8 to 20% by weight and preferably about 10 to 15% by weight of the total composition and the humectant in an amount from about 15–30% by weight and preferably about 20–28% by weight of the total composition, the oil phase being in an amount from about 50 to 77% by weight of the total composition. The oil phase comprises petrolatum in an amount of at least 40 to 70% by weight of the total composition, a water-in-oil emulsifier being generally in an amount from about 0.5 to 5% by weight of the total composition, and preferably 1 to 2% by weight of the total composition and, if present, the remainder comprising mineral oil.

GENERAL METHOD FOR MAKING THE TRANSLUCENT EMULSION OF THIS INVENTION

In producing the translucent water-in-oil emulsions of this invention the following procedure which may be used includes the employment of conventional preservatives which protect against spoilage by contaminating microorganisms.

PHASE A (oil phase) is formed by combining the appropriate amounts of petroleum jelly and the like (e.g. petroleum jelly and mineral oil) into an appropriate oil phase kettle. With agitation the mixture is heated until a clear liquid is obtained. Add a suitable oil soluble preservative (e.g. propylparaben) and mix until dissolved. To the clear liquid add a suitable amount of emulsifier with agitation.

Prepare phase B (water phase) in a suitable water phase kettle by first adding to the kettle the appropriate amount of water. Dissolve an appropriate water soluble preservative (e.g. methylparaben) with agitation. Add a suitable amount of humectant into the water phase and continue agitation until clear solution is obtained.

Add an appropriate dye to the water phase. The water, humectant, dye and any other components of the water phase should be of such nature and in such amounts that the resulting water-phase of the emulsion to be produced will have a refractive index close to petroleum jelly i.e. 1.4 to 1.5, preferably 1.45 to 1.48.

The water phase is slowly transferred to the oil phase kettle with proper high speed agitation, preferably a side scraper with homo-head attached to the kettle.

After addition of the water phase, mixing is continued for 15 minutes to form a uniform water-in-oil emulsion. The resulting emulsion is homogenized at 70° C. for 20–30 minutes while controlling aeration during homogenizing. After the homogenization is complete the batch is cooled to 50° C., using slow cooling by gradually adding water to the jacket. If one cools too quickly the product will solidify on the walls of the vessel which may require scraping the walls.

In forming the translucent water-in-oil emulsion of this invention the petroleum jelly and the like component may be the well known white petrolatum USP which has been widely used for its emollient, softening, soothing and protective characteristics as well as white petrolatum modified with mineral oil.

Any humectant which forms water-in-oil emulsions and which when in the water phase with water and the other water-soluble materials gives a refractive index resembling or matching that of petroleum jelly may be used. Examples of such humectants are glycerine, sorbitol, polyethylene glycol, propylene glycol, polysaccharides, corn syrup, sodium pyrrolidone carboxylic acid, sodium lactate and derivatives, monosodium glutamate, polyols, urea and derivatives and natural honey.

A preferred humectant is the polysaccharide sucrose. Other useful polysaccharides and fructose, glucose, maltose, etc.

Examples of suitable water-in-oil emulsifiers that may be used in accordance with this invention are polyglycerol - 4 cocoate, polyglycerol - 10 decaoleate, polyglycerol - 10 decalinoleate, polyglycerol - 2 diisostearate, polyglycerol - 3 diisostearate, polyglycerol - 6 dioleate, polyglycerol - 6 distearate, polyglycerol - 4 isostearate, polyglycerol - 3 oleate, polyglycerol - 4 oleate, polyglycerol - 2 sequiisostearate, polyglycerol - 2 sesquioleate, polyglycerol- 3 stearate, polyglycerol - 4 stearate, polyglycerol - 8 stearate, polyglycerol - 10 tetraoleate and polyglycerol - 2 tetraoleate.

In the emulsion of the present invention the water and humectant impart a moisturizing effect on the skin.

Any coloring agent that is used should preferably be one that will contribute to the emulsion matching the color of petroleum jelly.

SPECIFIC DESCRIPTION OF THE INVENTION

The following are specific examples of the translucent water-in-oil emulsions of this invention. In the examples, the polyglycerol oleate and polyglycerol isostearate are manufactured by the WITCO CHEMICAL CO.

FORMULATION SAMPLES OF TRANSLUCENT PETROLEUM JELLY WATER IN OIL EMULSIONS

Example I

|  | % By Wt. |
|---|---|
| Petroleum Jelly | 50.00 |
| Mineral Oil | 14.00 |
| Polyglycerol 3-Oleate | 1.00 |
| Sucrose USP | 20.00 |
| Preservatives | 0.20 |
| Water | 14.80 |
|  | 100.00% |

Example II

|  | % By Wt. |
|---|---|
| Petroleum Jelly | 50.00 |
| Mineral Oil | 14.00 |
| Polyglycerol Isostearate | 1.00 |
| Sucrose USP | 20.00 |
| Preservatives | 0.20 |
| Water | 14.80 |
|  | 100.00% |

Example III

|  | % By Wt. |
|---|---|
| Petroleum Jelly | 50.00 |
| Mineral Oil | 14.00 |
| Polyglycerol Isostearate | 1.00 |
| Sodium Pyrrolidone Carboxylic Acid | 15.00 |
| Sucrose USP | 5.00 |
| Preservatives | 0.20 |
| Water | 14.80 |
|  | 100.00% |

Example III

|  | % By Wt. |
|---|---|
| Petroleum Jelly | 50.00 |
| Mineral Oil | 14.00 |
| Polyglycerol Isostearate | 1.00 |
| Sodium Pyrrolidone Carboxylic Acid | 15.00 |
| Sucrose USP | 5.00 |
| Preservatives | 0.20 |
| Water | 14.80 |
|  | 100.00% |

Example IV

|  | % By Wt. |
|---|---|
| Petroleum Jelly | 50.00 |
| Polyglycerol Oleate | 1.00 |
| Sorbitol (100% Powder) | 28.80 |
| Preservatives | 0.20 |
| Water | 20.00 |
|  | 100.00% |

Example V

|  | % By Wt. |
|---|---|
| Petroleum Jelly | 64.00 |
| Polyglycerol Isostearate | 1.00 |
| Sucrose USP | 20.00 |
| Preservatives | 0.20 |
| Water | 14.80 |
|  | 100.00% |

Example VI

|  | % By Wt. |
|---|---|
| Petroleum Jelly | 50.00 |
| Polyglycerol Oleate | 1.00 |
| Hydrogenated Glucose Syrups | 28.80 |
| Preservatives | 0.20 |
| Water | 20.00 |
|  | 100.00% |

Example VII

| | % By Wt. |
|---|---|
| Petroleum Jelly | 48.50 |
| Paraffin Wax | 0.50 |
| Mineral Oil 200 SUS | 3.00 |
| Polyglycerol Oleate | 1.00 |
| Sorbitol (70% Solution) | 39.00 |
| Preservatives | 0.20 |
| Water | 7.80 |
| | 100.00% |

Example VIII

| | % By Wt. |
|---|---|
| Petroleum Jelly | 53.80 |
| Polyglycerol Isostearate | 1.00 |
| Urea | 30.00 |
| Preservatives | 0.20 |
| Water | 15.00 |
| | 100.00% |

Example IX

| | % By Wt. |
|---|---|
| Petroleum Jelly | 68.80 |
| Polyglycerol Isostearate | 1.00 |
| Monosodium Glutamate | 15.00 |
| Preservatives | 0.20 |
| Water | 15.00 |
| | 100.00 |

Example X

| | % By Wt. |
|---|---|
| Petroleum Jelly | 48.00 |
| Mineral Oil | 3.50 |
| Polyglycerol Oleate | 1.00 |
| Sorbitol (70% solution) | 39.00 |
| Glycerine | 24.50 |
| Preservatives | 20.00 |
| Water | 2.80 |
| | 100.00 |

Example XI

| | % By Wt. |
|---|---|
| Petroleum Jelly | 48.5 |
| Mineral Oil 200 SUS | 3.5 |
| Polyglycerol Oleate | 1.00 |
| Propylene Glycol | 20.00 |
| Sorbitol (70% solution) | 24.00 |
| Preservatives | 0.20 |
| Water | 2.80 |
| | 100.00 |

By combining the humectant cited in Examples I to XI, e.g., surcrose, sorbitol, glycium, propylene glycol, urea, sodium pyrrolidone carboxylic acid, monosodium glutamate and hydrogenated glucose syrups you can also obtain translucent emulsions of similar properties.

What is claimed is:

1. A translucent water-in-oil emulsion having the same general appearance and feel as petroleum jelly comprising an aqueous phase, said aqueous phase comprising water in an amount from 8% to 20% by weight of the total composition and a humectant in an amount from about 15% to 30% by weight of the total compositon, an oil phase in an amount of about 50% to 77% by weight, said oil phase comprising petroleum jelly in an amount from about 40% to 70% by weight of the total composition and a water-in-oil emulsifying agent in an amount needed to form the water-in-oil emulsion, said aqueous phase having a refractive index in essentially the same range as the oil phase to produce the translucent water-in-oil emulsion.

2. A translucent water-in-oil emulsion according to claim 1, wherein mineral oil is present.

3. A translucent water in oil emulsion according to claim 1 wherein the water phase contains water in an amount from about 10 to 15% by weight of the total composition and the humectant is in an amount from about 20–28% by weight of the total composition.

4. A translucent water-in-oil emulsion according to claims 1 or 3 wherein the water-in-oil emulsifier is in an amount from about 0.1 to 5% by weight of the total composition.

5. A translucent water-in-oil emulsion according to claims 1 or 3 wherein the water-in-oil emulsifying agent is in an amount from 1 to 2% by weight of the composition.

6. A translucent water-in-oil emulsion according to claim 1 or 3 wherein the emulsifier is selected from the group consisting of polyglycerol - 4 cocoate, polyglycerol - 10 decaoleate, polyglycerol - 10 decalinoleate, polyglycerol - 2 diisostearate, polyglycerol - 3 diisostearate, polyglycerol - 6 dioleate, polyglycerol - 6 distearate, polyglycerol - 4 isostearate, polyglycerol - 3 oleate, polyglycerol - 4 oleate, polyglycerol - 2 sequiisostearate, polyglycerol - 2 sequioleate, polyglycerol - 3 stearate, polyglycerol - 4 stearate, polyglycerol - 8 stearate, polyglycerol - 10 tetraoleate and polyglycerol - 2 tetraoleate.

7. A translucent water-in-oil emulsion according to claims 1 or 3 wherein the humectant is selected from the group consisting of glycerine, sorbitol, polyethylene glycol, propylene glycol, polysaccharides, corn syrup, sodium pyrrolidone carboxylic acid, sodium lactate and derivatives, monosodium glutamate, polyols, urea and derivatives and natural honey.

8. A translucent water-in-oil emulsion according to claims 1 or 3 wherein the humectant is a polysaccharide selected from the groups consisting of sucrose, fructose, glucose and maltose.

9. A translucent water-in-oil emulsion according to claims 1 or 3 wherein the humectant is a DL2-pyrrolidone-5 carboxylic acid.

10. A translucent water-in-oil emulsion according to claims 1 or 3 wherein the water-in-oil emulsifier is polyglycerol isostearate.

* * * * *